United States Patent
Orcutt et al.

(10) Patent No.: US 9,572,542 B2
(45) Date of Patent: Feb. 21, 2017

(54) ESTIMATING PHARMACOKINETIC PARAMETERS IN IMAGING

(71) Applicants: INVICRO, LLC, Boston, MA (US);
Kelly Davis Orcutt, Somerville, MA (US); John Hoppin, Boston, MA (US); Jacob Hesterman, Boston, MA (US); Christian Lackas, Cologne (DE)

(72) Inventors: Kelly Davis Orcutt, Somerville, MA (US); John Hoppin, Boston, MA (US); Jacob Hesterman, Boston, MA (US); Christian Lackas, Cologne (DE)

(*) Notice: Subject to any disclaimer, the term of this patent is extended or adjusted under 35 U.S.C. 154(b) by 184 days.

(21) Appl. No.: 14/405,901

(22) PCT Filed: Jun. 7, 2013

(86) PCT No.: PCT/US2013/044767
§ 371 (c)(1),
(2) Date: Dec. 5, 2014

(87) PCT Pub. No.: WO2013/185066
PCT Pub. Date: Dec. 12, 2013

(65) Prior Publication Data
US 2015/0297160 A1    Oct. 22, 2015

Related U.S. Application Data

(60) Provisional application No. 61/656,811, filed on Jun. 7, 2012.

(51) Int. Cl.
*A61B 6/00* (2006.01)
*A61B 6/03* (2006.01)
(Continued)

(52) U.S. Cl.
CPC ............. *A61B 6/501* (2013.01); *A61B 5/0071* (2013.01); *A61B 5/055* (2013.01); *A61B 5/4064* (2013.01);
(Continued)

(58) Field of Classification Search
CPC ..................... A61B 2503/40; A61B 2576/026; A61B 5/0071; A61B 5/055; A61B 5/4064; A61B 5/7278; A61B 6/032; A61B 6/037; A61B 6/481; A61B 6/501; A61B 6/506; A61B 6/5217; G06F 19/345; G06F 19/704
See application file for complete search history.

(56) References Cited

U.S. PATENT DOCUMENTS

2008/0183069 A1    7/2008  Fujimoto
2009/0190806 A1    7/2009  Muradyan
(Continued)

FOREIGN PATENT DOCUMENTS

WO    WO2012022812 A1    2/2012

OTHER PUBLICATIONS

International Search Report for PCT/US2013/044767, published on Mar. 13, 2014.
(Continued)

*Primary Examiner* — Mark Remaly
(74) *Attorney, Agent, or Firm* — Duane Morris LLP (57) ABSTRACT

A method of estimating a parameter of physiological significance in the central nervous system (CNS) is provided. The method comprises (a) providing one or more images of the brain or cerebral spinal fluid (CSF) in a subject to whom a dose of a contrast agent (CA) has been administered; (b) determining, using a computer equipped with image processing software, the concentration or relative concentration of the agent in a region or regions of interest in the brain or CSF, thereby generating concentration data; (c) describing
(Continued)

the time-based behavior of concentrations of CA within the brain or CSF using a pharmacokinetic model that is based on a set of pharmacokinetic model parameters; and (d) fitting, using computer code, the pharmacokinetic model to the concentration data, varying one or more parameters, wherein the best fit estimates a parameter of physiological significance in the CNS.

18 Claims, 8 Drawing Sheets

(51) Int. Cl.
  *A61B 5/00*    (2006.01)
  *A61B 5/055*   (2006.01)
  *G06F 19/00*   (2011.01)

(52) U.S. Cl.
  CPC ............. *A61B 5/7278* (2013.01); *A61B 6/032* (2013.01); *A61B 6/037* (2013.01); *A61B 6/481* (2013.01); *A61B 6/506* (2013.01); *A61B 6/5217* (2013.01); *G06F 19/345* (2013.01); *G06F 19/704* (2013.01); *A61B 2503/40* (2013.01); *A61B 2576/026* (2013.01)

(56) References Cited

U.S. PATENT DOCUMENTS

2010/0284934 A1  11/2010 El-Agnaf
2011/0181283 A1   7/2011 Grinstead

OTHER PUBLICATIONS

Written Opinion of the International Searching Authority for PCT/US2013/044767, mailed on Nov. 19, 2013.

ESTIMATING PHARMACOKINETIC PARAMETERS IN IMAGING

CROSS-REFERENCE TO RELATED APPLICATIONS

This application is a United States national phase application of international application number PCT/US2013/044767, filed under 35 U.S.C. §371, filed on Jun. 7, 2013, which claims the benefit of the filing date of U.S. Provisional Application No. 61/656,811, which was filed Jun. 7, 2012. The entire content of these prior applications is hereby incorporated by reference herein.

FIELD OF THE INVENTION

The present invention relates to molecular imaging and mathematical modeling and more particularly to methods that use these techniques in concert to assess various physiological parameters relevant to drug development and patient treatment. For example, the present methods can be used to estimate capillary to brain parenchyma permeability, cerebral spinal fluid (CSF) to brain parenchyma transport rate, and binding site concentration from molecular imaging data.

BACKGROUND

It is well known that studies are conducted in animals during preclinical drug development to determine in vivo pharmacokinetics, pharmacodynamics, efficacy, and toxicity, and that these studies are used in an effort to predict effective drug concentrations in humans. Advancements in small-animal imaging technology over the past decade have enabled quantitative assessment of dynamic in vivo distribution of radiolabeled compounds (Smith-Jones et al., *Nature Biotechnol.* 22:701-706, 2004; Robinson et al., *Cancer Res.* pp. 1471-1478, 2005; Cai et al., *Eur. J. Nucl. Med. Mol. Imaging* 34:850-858, 2007; Cai et al., *J. Nucl. Med.* 48:304-310, 2007; Sosabowski et al., *Star* 40:2082-2089, 2009) as well as quantitative sub-organ analysis (Hoppin et al., *J. Pharmacol. Exp. Ther.* In press). Designing, performing, and interpreting these imaging studies is a complex, interdisciplinary effort. Many parameters define the results of an imaging study including isotope selection, radiolabeling chemistry, specific activity, injected activity, compound pharmacology, the animal model, imaging time points, imaging scan time, reconstruction algorithms, image processing, and others.

In the clinic, molecular imaging (primarily SPECT and PET) is a medical imaging technique in which a human subject can be imaged in two- or three-dimensions to quantitatively or semi-quantitatively determine the distribution of an administered exogenous contrast agent.

Existing approaches to analysis of PET and SPECT in the clinic include drawing regions of interest and determining the concentration or relative concentration of the contrast agent in the region of interest. However, it is unclear how the concentration of contrast agent is related to contrast agent and in vivo transport properties.

SUMMARY

The present invention encompasses methods for estimating physiological parameters relevant to drug development and patient treatment from imaging data. The present methods can be used to estimate brain, CSF and contrast agent properties from molecular imaging data, parameters which may be used in accelerating the development of brain- and central nervous system (CNS)-targeting therapeutics, improving patient selection and stratification for clinical trials and treatment regimes, and monitoring patient responses to treatment. Thus, the featured methods can be used to improve not only the design and preclinical development of therapeutics, but also the clinical use of brain- and CNS-targeting therapeutics and complementary biomarkers. More specifically, the methods allow in vivo molecular imaging to be used to quantitatively estimate physiological parameters such as antigen expression levels, contrast agent internalization rate, brain permeability, CSF to brain transport rate, and contrast agent binding affinity. Furthermore, brain-region quantitative analysis allows characterization of the variability of these properties in vivo in different regions of the brain.

Parameters such as those mentioned above are often unknown or may be different in an in vivo versus an in vitro or ex vivo context. To estimate these parameters (and others) in vivo, we have developed a method to fit a pharmacokinetic model (varying one or more parameters) to experimental in vivo imaging data. Accordingly, the present invention features methods in which mathematical models are used in conjunction with imaging data to estimate parameters of physiological significance. Our methods use computer code to fit a model to imaging data. The best fit estimates a parameter or multiple parameters of physiological significance. Accordingly, the present invention is based, in part, on our development of methods that involve providing one or more images of a biological tissue that has been exposed to an imaging agent (e.g., the images can be obtained at set temporal intervals, which may be regular or irregular) and determining, using a computer equipped with image processing software, the concentration or relative concentration of the imaging agent in a region of interest in the tissue. A user then fits, using computer code, a pharmacokinetic model to the concentration data, varying one or more parameters so the best fit estimates a parameter or parameters of physiological significance. More specifically, in one embodiment, the average SUV (standardized uptake value) within the entire brain ROI (region of interest) or sub-regions of the brain can be determined from imaging reconstruction, analysis, and quantification. The SUV-time data is then fit to the model varying antigen density and brain permeability (with known input parameters describing the ligand (affinity, specific activity, etc.) and the imaging study (time points, injected activity, body weight, arterial input function)).

In another aspect, the invention features a software system for performing the methods described above (e.g., for fitting a pharmacokinetic model to data).

One advantage of the present methods is their applicability to a variety of contexts. They can be used to predict the pharmacokinetics of brain- and CNS-targeted agents and to estimate select in vivo brain and CSF parameters (binding affinity, antigen expression, permeability, and internalization rate) from imaging data. The techniques are also applicable across species and translatable from the lab to the clinic. Accordingly, the subject can be any animal, including a rodent, dog, or non-human primate, useful in preclinical analysis. In other embodiments, the subject can be a human subject or patient. Further, our models provides several important capabilities: (1) the connection of in vitro/ex vivo characterization of new compounds and in vivo brain imaging studies, (2) the estimation of brain properties in vivo from molecular imaging data, and (3) characterization of free, bound, and internalized drug fractions in the brain and in different brain regions from imaging data.

DETAILED DESCRIPTION

The uptake of a given compound (e.g., a radiolabeled compound that can be imaged) by a tissue (e.g., a brain) and the distribution of the compound in the tissue depends on a variety of parameters including, but not limited to, binding affinity, the concentration of binding sites within the tissue, and the capillary permeability of the compound in the tissue. PET, SPECT, MR and fluorescence imaging can be used to estimate the distribution of a compound (e.g., imaging agent) within a subject (e.g., a mammal such as a rodent, non-human primate or human). Image analysis techniques are applied to composite images in order to quantify the uptake or concentration of an imaging agent. For example, a radiologist can classify the brain and regions of the brain within a PET image and a region of interest can be created to segment said brain within the image. The values of the image within the segmented brain provide means of estimating the uptake and concentration of a pharmaceutical labeled with a positron emitter (e.g. 18F-AV-45, and FDA approved PET radiopharmaceutical). An array of qualitative metrics for the distribution of radiopharmaceuticals are employed in nuclear medicine, most commonly some weighted form of the percent injected dose (% ID) such as the standardized uptake value (SUV) used extensively in PET imaging.

Estimating physiologically relevant brain parameters in vivo is challenging. Brain-targeted molecular imaging agents offer a great advance in this effort, though in practice their output is most often limited to uptake and concentration within the brain at a fixed point in time. Imaging using multiple modalities (e.g. PET and MRI or PET and CT) often offers advanced anatomical information about the brain such as volume and morphology. Combining this anatomical and functional imaging has been and continues to be a boon to neurologists, but is again limited in terms of characterizing more advanced physiology. Dynamic imaging of such agents offers significant improvements, often enabling the estimation of transport rates across the blood brain barrier. The method put forward in this invention enables the estimation of a broader scope of understanding of brain physiology; most notably the antigen density in the brain, the internalization rate of the brain-targeting compound and the blood brain barrier permeability of the compound.

Figure 1:
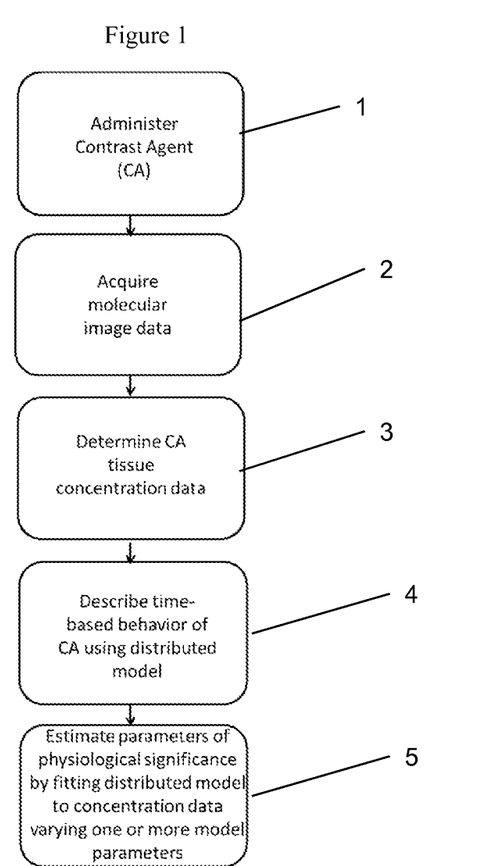
FIG. 1 is a flowchart illustrating a method for performing pharmacokinetic analysis in molecular imaging according to an exemplary embodiment of the present invention.

FIG. 1 illustrates a method for performing pharmacokinetic analysis in molecular imaging according to an exemplary embodiment described in detail below.

At step 1, a contrast agent is administered.

At step 2, molecular image data are acquired.

At step 3, CA tissue concentration data are determined.

At step 4, a model of the time-based behavior of the CA is described by the computer.

At step 5, parameters of physiological significance are determined by fitting the distributed model to the concentration data, varying one or more model parameters.

Specifically, we describe a method using a pharmacokinetic model of molecular transport in the brain and cerebral spinal fluid (CSF) and multiple time point SPECT or PET or MR or fluorescence imaging to quantitatively estimate an array of physiological parameters including the aforementioned number of binding sites in the brain, the internalization rate of the imaging agent and the brain permeability to name a few. The methods put forward can include the steps of providing one or more images at set temporal intervals of a subject who has been exposed to an imaging agent; determining, using a computer equipped with image processing software, the concentration or relative concentration of the agent in a region of interest in the tissue, thereby generating concentration data; and fitting, using computer code, a pharmacokinetic model to the concentration data, varying one or more parameters such that the best fit estimates a parameter of physiological significance. In another embodiment, brain permeability can be measured by other means (e.g. MR or CT imaging) and in this case, only a single SPECT or PET or MR or fluorescence image may be necessary to quantitatively estimate a physiological parameter such as the number of binding sites in the brain. In another embodiment, only a single SPECT or PET or MR or fluorescence image can be used to estimate a physiological parameter such as the number of binding sites in the brain by providing the model with a limited range of other parameters such as brain permeability from the literature.

The pharmacokinetic model may be a distributed model. Distributed models, i.e. models that describe spatial as well as temporal variations (Cheong et al., *Radiology* 232:921-930, 2004; Mescam et al., *IEEE Trans. Med. Imaging*, 29:699-707, 2010; and Kellen and Bassingthwaighte, *Am. J. Physiol. Heart Circ. Physiol.* 285:H1303-1316, 2003), while more physiologically relevant (Anderson and Bassingthwaighte, "Tracers in physiological systems modeling in Mathematical Modeling in Nutrition and Agriculture", Virginia Polytechnic Institute and State University, Roanoke, Va., 2006; Cheong, supra, and Kuikka et al., *Eur. J. Nucl. Med.* 18:351-362, 1991), have not yet been adopted widely by the preclinical and clinical research communities largely due to their mathematical complexity. For brain- and CNS-targeting compounds, it can often be advantageous to inject the compounds into the CSF space via intrathecal route of injection rather than intravenous. The use of mathematical models to simulate the transport and kinetics of a compound injected via intrathecal or intravenous routes and the subsequent brain and CSF uptake and distribution can aid in assessing the best route of injection and guide dose selection for clinical studies. For example, from the methods described here, one might predict brain and CSF distribution in humans from imaging data and subsequent parameter estimation in a relevant animal model of disease. For example, one or more preclinical images may be provided at set temporal intervals of a subject who has been exposed to a contrast agent; determining, using a computer equipped with image processing software, the concentration or relative concentration of the agent in a brain region of interest, thereby generating concentration data; and fitting, using computer code, a pharmacokinetic model to the concentration data, varying Bmax and permeability parameters such that the best fit estimates brain binding sites and brain permeability of the contrast agent. These brain parameters may then be used with the same pharmacokinetic model or a different one to predict the brain and CSF uptake and macro- and/or micro-distribution of the contrast agent in humans. In this case, while brain permeability and BMax would be assumed to remain the same, brain volume, CSF volume, and CSF flow rate parameters would be modified to human parameters. Using the brain parameters estimated by the animal study, the transport and brain targeting in humans can be predicted.

Figure 2:
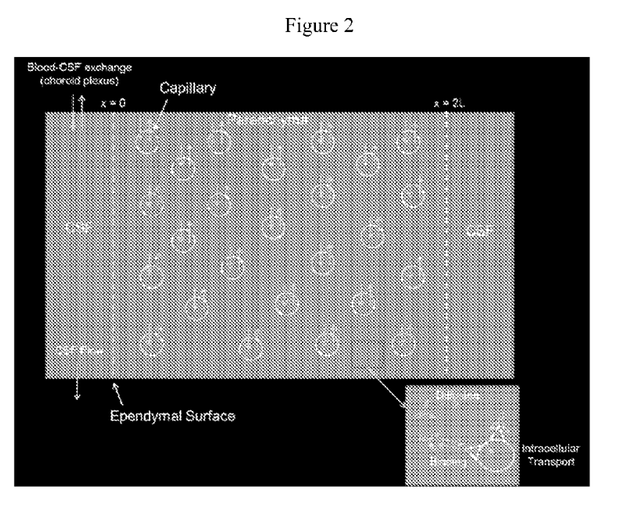
FIG. 2 is a schematic of a distributed model that describes the concentration of CA in the brain and CSF.
Figure 3:
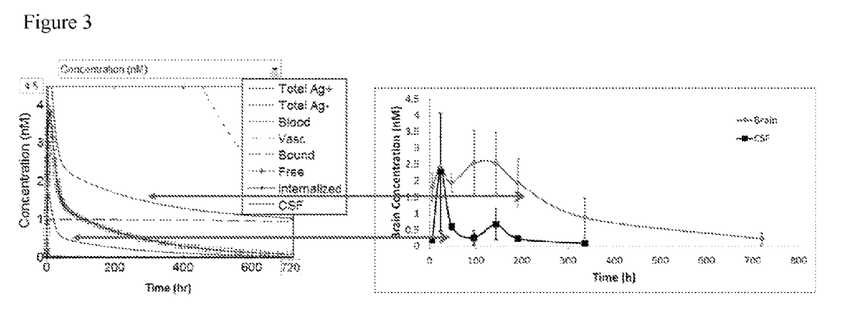
FIG. 3 shows plots of simulated data compared to experimental data (from Pepinsky et al. JPET, 2011). Simulated data (left) was generated using the distributed brain PK model described herein to simulate brain accumulation of an anti-LINGO-1 antibody. All model parameters were derived from Pepinsky et al. ($K_D$=0.02 nM, blood clearance, injected dose=30 mg/kg) and Poduslo et al. 2001 (PS/V=1.3×10$^{-7}$ for an antibody). Antigen density of LINGO-1 was assumed to be 1 nM.

The distributed model may be based on the below partial differential equations and boundary and initial conditions:

$$\frac{\partial C(x,t)}{\partial t} = D\frac{\partial^2 C(x,t)}{\partial x^2} + \frac{PS}{V}\left(C_P(t) - \frac{C(x,t)}{\varepsilon}\right) - k_{on}\frac{C(x,t)}{\varepsilon}T(x,t) + k_{off}B(x,t)$$

$$\frac{\partial B(x,t)}{\partial t} = k_{on}\frac{C(x,t)}{\varepsilon}T(x,t) - k_{off}B(x,t) - k_{int}B(x,t)$$

$$\frac{\partial T(x,t)}{\partial t} = R_s - k_{on}\frac{C(x,t)}{\varepsilon}T(x,t) + k_{off}B(x,t) - k_{int,T}B(x,t)$$

$$\frac{\partial I(x,t)}{\partial t} = k_{int}B(x,t) - k_{resid}I(x,t)$$

$$\frac{\partial C_{CSF}(t)}{\partial t} = -\frac{Q_{CSF}}{V_{CSF}}C_{CSF}(t) + \frac{D_E A}{V_{CSF}}\frac{\partial C(0,t)}{\partial x} + \frac{P_{BCSFB}S_{BCSFB}}{V_{CSF}}(C_P(t) - C_{CSF}(t))$$

$$\frac{\partial C(L,t)}{\partial x} = 0$$

$$C_{CSF}(t) = C(0,t)$$

wherein C denotes the free CA concentration in the brain parenchyma, B denotes the bound CA/antigen concentration in the brain parenchyma, T denotes the unbound antigen concentration in the brain parenchyma, I denotes the concentration of intracellular CA, $C_{CSF}$ denotes the concentration of CA in the CSF, D denotes the CA diffusion coefficient in brain parenchyma, $k_{on}$ denotes the CA/antigen association rate constant, $k_{off}$ denotes the CA/antigen dissociation rate constant, $\varepsilon$ denotes the CA void fraction in the parenchyma, $k_{int}$ denotes the internalization rate constant of the CA/antigen bound complex, $k_{int,T}$ denotes the internalization rate constant of the antigen, $k_{resid}$ denotes the rate of release of CA or CA signal from the intracellular compartment, $R_S$ denotes the antigen synthesis rate, L denotes the half-distance of the parenchymal thickness, A denotes the ependymal surface area, P denotes the capillary to brain permeability, S denotes the capillary surface area in the brain, V denotes the brain volume, $P_{BCSFB}$ denotes the blood/CSF barrier permeability, $S_{BCSFB}$ denotes the blood/CSF surface area, $V_{CSF}$ denotes the CSF volume, $D_E$ denotes the diffusion rate across the ependymal surface, and $C_P$ denotes the plasma concentration of the contrast agent as a function of time, also sometimes called an arterial input function.

Interstitial diffusivity (D), and void fraction ($\varepsilon$) can be measured experimentally (Thurber and Wittrup, Cancer Res. 68: 3334-3341, 2008, Yuan et al. Cancer Res. 55: 3752-3756, 1995). Interstitial diffusivity (D), and void fraction ($\varepsilon$) can also be estimated from the molecular weight of the contrast agent based on empirical relationships derived in the literature (Schmidt and Wittrup, Mol. Cancer Ther. 8:2861-2871, 2009). $k_{on}$ can be measured experimentally or calculated from the dissociation constant ($K_D$) and $k_{off}$ ($k_{on}=k_{off}/K_D$), or assumed to be typical for antibodies and antibody fragments ($10^5$–$10^6$ $M^{-1}$ $s^{-1}$). $k_{off}$ can be measured experimentally or calculated from $K_D$ and $k_{on}$ ($k_{off}=K_D \times k_{on}$). $k_{int}$ and $k_{int,T}$ can be measured experimentally (Schmidt et al. Cancer Immunol Immunother. 57:1879-1890, 2008) or varied within a physiological range. $k_{resid}$ depends on the isotope/fluorophore and labeling chemistry and can be measured experimentally (Press et al. Cancer Res 56: 2123-2129, 1996), or assumed to be equal to previous measurements reported in the literature for specific isotopes and labeling chemistry. PS/V and $P_{BCSFB}S_{BCSFB}/V_{BCSFB}$ can be measured experimentally in animal models or assumed to be equal to similar compounds reported in the literature (Poduslo et al. 2001). L and A can be measured experimentally from biopsy sample(s) or varied within a physiological range. $T_0$ can be measured experimentally from biopsy sample(s) or assumed to be varied within a physiological range. $T_0$ can also be estimated from Bmax (number of binding sites per cell) that can be measured experimentally and brain cell density (number of cells per volume of brain tissue): $T_0$=Bmax×cell density/Avogadro's number. $C_P$ can be measured experimentally from blood sample data or can be estimated from the image data. $R_S$ is calculated based on the input values $T_0$ and $k_{int,T}$ ($k_{int,T} \times T_0$).

The differential equations solve for C, B, I, T, and CSF, which represent the concentration of free CA, bound CA, internalized CA, free antigen, and concentration of CA in the CSF, respectively. For in vivo molecular imaging data, the total signal is a sum of the free, bound, and internalized contrast agent signal in the brain tissue as well as the contrast agent signal in the brain vascular space. From the total signal and the initial dose, specific activity, and brain size, the average concentration, % ID/g, % ID, activity, SUV, and brain to blood ratios can be calculated.

FIG. 2 is a schematic of the distributed model described by the equations above. CA can enter and leave the brain parenchyma through the capillaries. Within the parenchyma, CA can diffuse as well as bind and dissociate from antigen (T). Bound complex can internalize into the intracellular space of the cell. The ependymal surface is the boundary between the brain parenchyma and the CSF. L is the average half-distance of parenchymal thickness. CSF exhibits bulk flow. There is also blood-CSF exchange in the choroid plexus where CA can enter and leave the CSF from the blood.

The model can be implemented in MATLAB using the method of lines to discretize the spatial derivatives in the equations. The resulting ordinary differential equations can be solved using Runge-Kutta methods or similar method, or an ordinary differential equation solver in MATLAB (such as ODE15s or ODE23). The model can be fit to image data using nonlinear optimization (such as with the Quasi-Newton or Nelder-Mead algorithms) to determine the parameter or parameters that result in the best fit of the model simulation to the image data.

Figure 4:
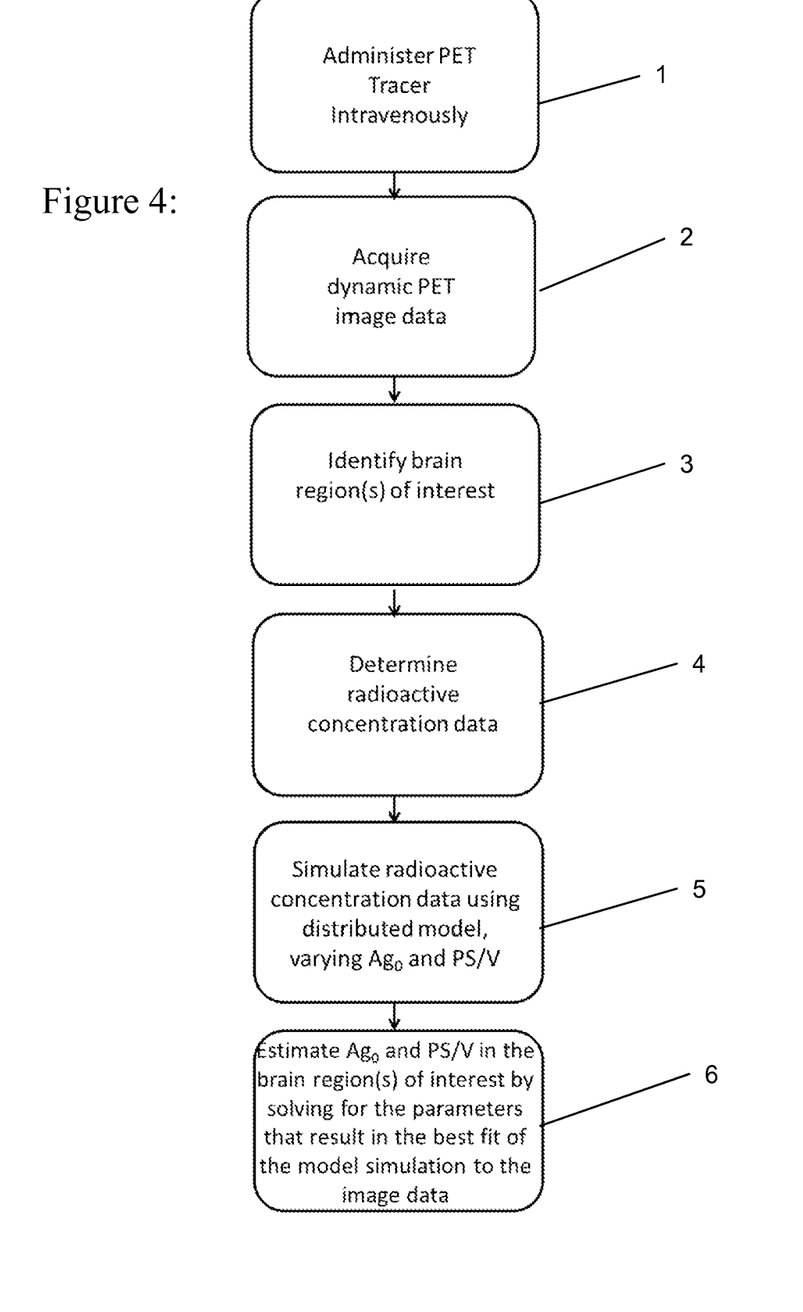
FIG. 4 is a flowchart illustrating a method for estimating antigen density (Ag0) and capillary to brain parenchema permeability.

FIG. 4 is a flowchart summarizing a method for estimating antigen density ($T_0$) and brain permeability (PS/V) using a PET tracer and resulting PET image data according to an exemplary embodiment of the present invention described in greater detail below.

At step 1, a PET tracer is administered.

At step 2, dynamic PET image data are acquired. In some embodiments, the PET image data are stored in a non-transitory, computer readable storage medium.

At step 3, a brain region of interest is identified.

At step 4, radioactive concentration data are determined by the programmed computer, based on the image data. The radioactive concentration data are stored to the same (or another) non-transitory, computer readable storage medium.

At step 5, the radioactive concentration data are simulated in the programmed computer, using a distributed model, varying $T_0$ and PS/V.

At step 6, $T_0$ and PS/V in the brain region of interest are estimated by the programmed computer solving for the parameters that result in the best fit of the model simulation to the image data.

The contrast agents suitable for use in the present methods can be readily selected by one of ordinary skill in the art from those currently available and in current use as well as those developed at a later time. The currently available contrast agents include those that are commercially available. As noted, the contrast agent can be linked to a moiety (e.g., a peptide moiety) that binds a brain target (i.e., a moiety expressed, and preferably selectively expressed, by a neuron). The moiety may mimic a therapeutic agent (by, for example, its ability to bind a brain target) or it may be a therapeutic or potential therapeutic agent per se (including a small organic compound and a biotherapeutic, such as an antibody or other protein-based binding agent). For example, where the present methods are used to determine which of a plurality of potential therapeutic agents to advance from a pre-clinical to a clinical trial, one can label each of the potential therapeutic agents with a contrast agent and administer the labeled therapeutic agent to an animal model (e.g., a mouse having a type of neurodegenerative disease to be treated with the potential therapeutic agent). Following administration, and the procurement of images of the brain, one would then subject those images to the methods described herein to determine which of the potential therapeutic agents performed best with respect to a parameter of physiological significance (e.g., brain uptake that is due, for example, to brain permeability, high antigen expression and/or a high binding affinity).

Human brain targets are well studied in the art, and one can readily select a target of interest. For example, researchers and clinicians working on neurodegenerative treatments can use a contrast agent linked to a moiety that targets amyloid beta, Tau, LINGO-1, dopamine, serotonin, alpha synuclein, TDP-43, SOD-1 or GABA, among others. FDA-approved and investigational contrast agents include florbetapir (18F-AV45), 11C-PIB, 11C-ADAM, 11C-AFM, 11C-DAPA, 11C-McN5652, 11C-NS 4194, 11C-DASB, 18F-DOPA, 123I-beta-CIT, 123I-iomazenil, 18F-flumazenil, among others.

Once a potential therapeutic agent is selected for a clinical trial, one can continue to use the present methods to determine the agent's performance in humans suffering from a given disease. Once launched as a therapeutic, the response of individual patients can be monitored to determine whether the therapeutic is having the desired effect or whether an alternate course should be prescribed. Accordingly, the present methods include those in which the analyses described herein are carried out before a patient begins treatment and during the course of treatment to determine efficacy.

Currently, immunohistochemistry (IHC) is the most commonly used test to assess tumor antigen expression levels. IHC test scores are used in treatment planning. For example, patients with HER2-positive scores (a score of 2+ to 3+ on a scale of 0 to 3+) tend to respond favorably to HER2-targeted therapies such as Herceptin. For patients with neurodegenerative diseases, unfortunately, it is very difficult and dangerous to obtain brain samples for IHC analysis. Therefore, this is typically not performed in practice. The integration of imaging with modeling and simulation described herein thus enables the estimation of brain parameters not previously available to neurologists. In one embodiment, image data is used to quantitatively assess amyloid beta levels in the brain of a subject and from this assessment, a patient may be selected to receive a targeted therapy based on the quantitative amyloid beta level. For example, if the amyloid beta level is estimated to be greater than a predetermined cut point then the patient would be selected to receive the therapy. In another embodiment, image data is used to quantitatively assess amyloid beta expression level in the brain of a subject and from this assessment, a patient may be selected to be enrolled in a clinical trial based on the quantitative amyloid beta level. For example, if the amyloid beta level is estimated to be greater than a predetermined cut point then the patient would be enrolled in the trial.

Figure 5:
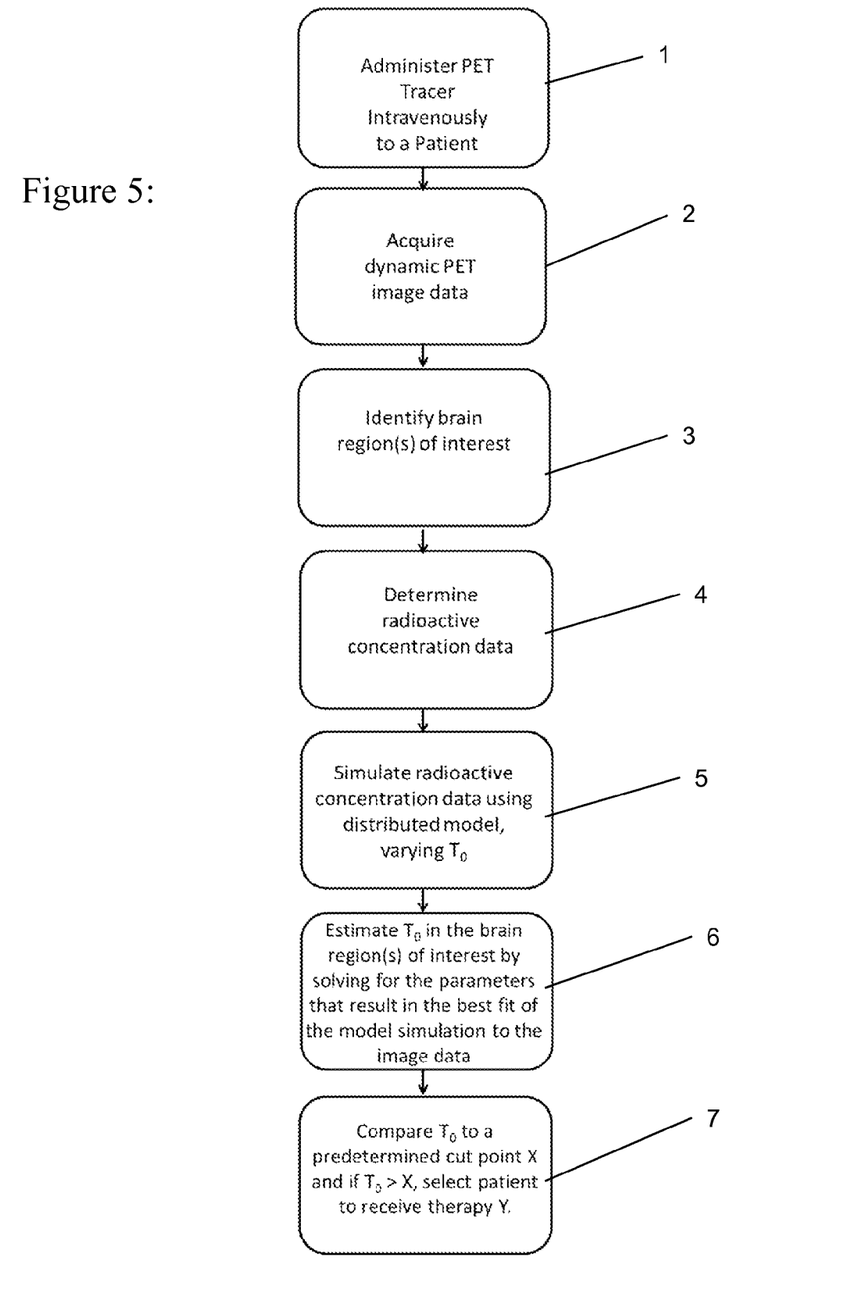
FIG. 5 is a flowchart summarizing the method for estimating amyloid beta density ($T_0$) using a PET tracer and resulting PET image data and using the estimated amyloid beta density to decide if the patient is to receive a particular therapy.

FIG. 5 is a flowchart summarizing the method for estimating amyloid beta density ($T_0$) using a PET tracer and resulting PET image data and using the estimated amyloid beta density to decide if the patient is to receive a particular therapy according to an exemplary embodiment of the present invention.

At step 1, a PET tracer is administered.

At step 2, dynamic PET image data are acquired. In some embodiments, the PET image data are stored in a non-transitory, computer readable storage medium.

At step 3, a brain region of interest is identified.

At step 4, radioactive concentration data are determined by the programmed computer, based on the image data. The radioactive concentration data are stored to the same (or another) non-transitory, computer readable storage medium.

At step 5, the radioactive concentration data are simulated in the programmed computer, using a distributed model, varying $T_0$.

At step 6, $T_0$ in the brain region of interest is estimated by the programmed computer solving for the parameters that result in the best fit of the model simulation to the image data.

At step 7, $T_0$ is compared to a predetermined cut point X and if $T_0$ is greater than X ($T_0 > X$) then the patient is selected to receive a particular therapy Y.

Numeric parameters derived from image data, e.g. cardiac ejection fraction, are in turn used to classify the disease state through a variety of decision strategies. One method to determine cardiac ejection fraction uses administered technetium-99m-pertechnetate followed by imaging the heart with a gamma camera. The patient's heart beat is used to gate the acquired image data resulting in a series of images of the heart at different stages of the cardiac cycle. The images show the blood pools in the chambers of the heart and can be computationally interpreted to calculate the ejection fraction.

In various embodiments, numeric parameters are calculated by the programmed computer. In addition to estimating the existence and prevalence of disease burden within a subject, estimating an array of parameters describing the numerical status of the brain during the diagnostic stage and throughout therapy offers physicians and researchers means of measuring the efficacy of their therapy strategy.

Determining the optimal imaging protocol for a study is a complex problem. The ability to predict, even roughly, the pharmacokinetics for an imaging agent within the brain and CSF offers considerable advantage when designing such a protocol.

Figure 6:
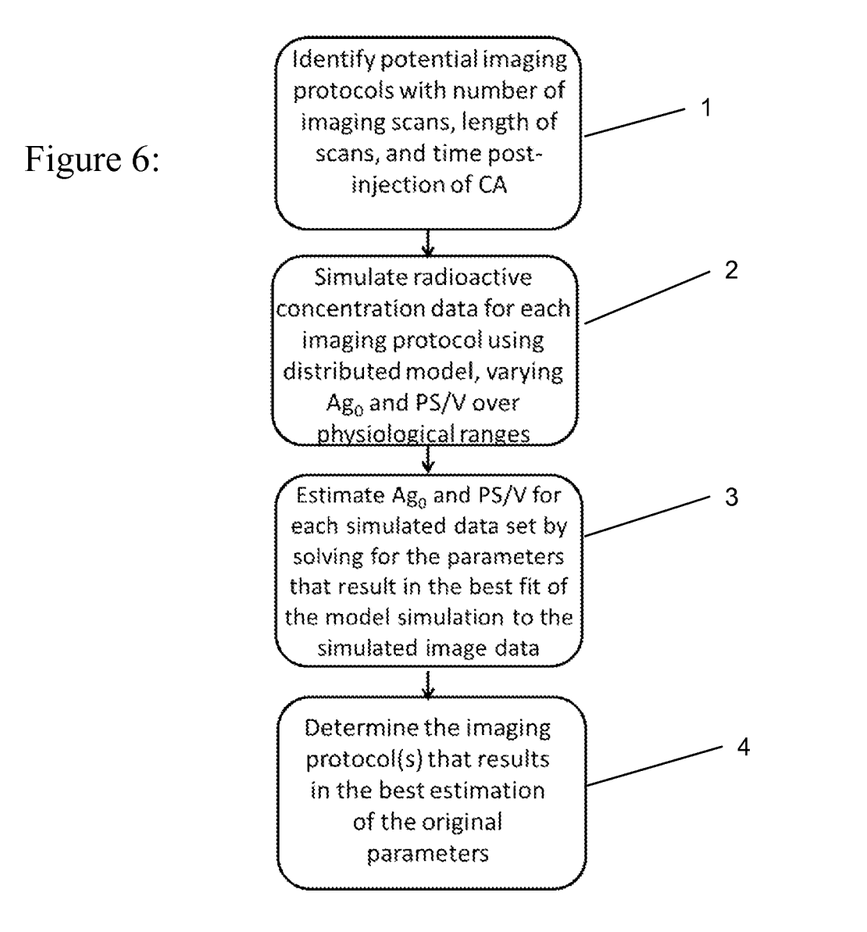
FIG. 6 is a flowchart illustrating a method for identifying an imaging protocol or protocols that results in best estimation of brain parameters.

FIG. 6 is a flowchart illustrating a method for identifying an imaging protocol or protocols that result in best estimation of brain parameters according to an exemplary embodiment of the present invention, described in detail below.

At step 1, potential imaging protocols are identified with a number of imaging scans, length of scans, and time post injection of contrast agent.

At step 2, radioactive concentration data are simulated in the programmed computer, for each imaging protocol using a distributed model, varying $T_0$ and PS/V over physiological ranges.

At step 3, $T_0$ and PS/V are estimated by the programmed computer for each simulated data set by solving for the parameters that result in the best fit of the model simulation to the simulated image data.

At step 4, the programmed computer determines the imaging protocol that results in the best estimation of the original parameters.

In FIG. 6, an approach is presented using the methods here to determine the optimal imaging protocol for a given study based on a set or sets of model parameters. For example, the above parameters for a specific target may be used to generate simulations of brain uptake as a function of time for varying $T_0$ and PS/V over physiological ranges for different possible imaging protocols (i.e. number of image scans, and time and duration of imaging scans). Physiological ranges for $T_0$ and PS/V may be 0-500 nM and $0.01 \times 10^{-6}$-$100 \times 10^{-6}$, respectively. Namely, one can for example select 10 values of $T_0$ and 10 values of PS/V from the above ranges for a total of 100 combinations of $T_0$ and PS/V. For each of these 100 pairs of $T_0$ and PS/V one can generate a curve for the predicted uptake curve of the imaging agent within the brain (a "time-activity curve") using the method and a computer. One can then have a set of parameters describing the imaging protocol, i.e., number of imaging scans, time post-injection of the imaging scans and the duration of the imaging scans. In general, these parameters are constrained by practical concerns. One can, however, determine 100 possible imaging protocols for example as defined by these three parameters: number of scans, time post-injection of scan and duration of scan. Given a predicted time-activity curve from the model and an imaging protocol, one can use the value on the predicted time-activity curve at each scheduled time in the protocol as the expected value for the uptake in the brain in an experiment. One can, for example, use the scan duration at each time to determine the standard variation of the estimate of the uptake of the imaging agent in an experiment. Given an expected value and a standard deviation for the brain uptake at each imaging time point in an experiment, one can use a computer to generate random samples for a given time-activity curve. In order to find the optimal imaging protocol, one can then run a simulation using a computer in which they generate many (e.g. 100, 1000, or other number) simulated experiments for each of the possible imaging protocols. Given this simulated experimental data, one can estimate $T_0$ and PS/V by fitting the model to the simulated brain uptake data. One can compare the estimates of $T_0$ and PS/V to the true values of $T_0$ and PS/V used to simulate the experimental data using, for example, the square root of the mean-squared error between the true and estimated values. For each of the 100 possible combinations of $T_0$ and PS/V, one can rank the 100 possible imaging protocols performance for estimating $T_0$ and PS/V according to the average of the root-mean-squared error values. One can select the imaging protocol that provides the best estimates of $T_0$ and PS/V across all 100 possible combinations of $T_0$ and PS/V. The imaging protocol that provides the best estimate of $T_0$ and PS/V can be defined as the optimal imaging protocol.

In addition to using the described method to estimate parameters of physiological significance, a modification of the method can be used in drug development to 1) select the best therapeutic candidate among a set of candidates and 2) to guide dose selection for human studies. In one embodiment, a series of drug candidates can be detectably labeled (e.g., radiolabeled) and administered to a relevant animal model. The in vivo distribution of the drug candidates can be determined over time using an imaging technique such as SPECT, PET, ex vivo counting of resected tissues, or autoradiography. The experimentally determined in vivo distribution of the drug candidates can be compared to that predicted by the model to validate the model. The model can then be used to simulate and predict the in vivo distribution of the drug candidates in a human. The candidate that is expected to perform best (e.g., the candidate that exhibits the highest brain or CSF concentration) would then be selected from the series of candidates for further development.

Figure 7:
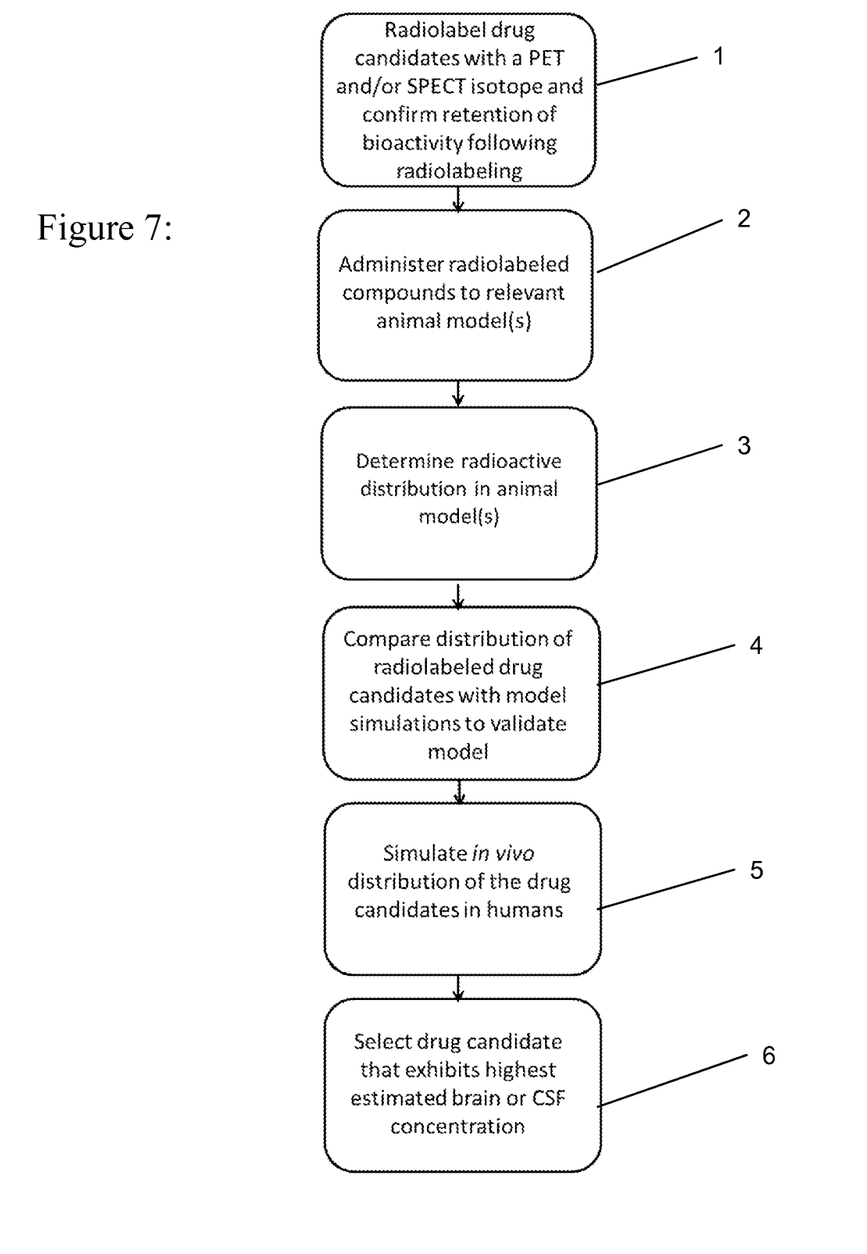
FIG. 7 is a flowchart summarizing the method to select the best therapeutic candidate among a set of candidates.

FIG. 7 is a flowchart summarizing the method to select the best therapeutic candidate among a set of candidates.

At step 1, drug candidates are radiolabeled with a radioisotope and bioactivity is confirmed following radiolabeling.

At step 2, radiolabeled drug candidates are administered to relevant animal model(s).

At step 3, the radioactive distribution in the animal model(s) is determined.

At step 4, the experimental radioactive drug distributions are compared with model simulations to validate the model.

At step 5, the model is used to simulate the in vivo distribution of the drug candidates in human patients.

At step 6, the drug candidate that exhibits the highest estimated drug or CSF concentration is selected for further development.

In another embodiment, one can use a modification of the described method to guide dose selection for human studies. One can have a set of parameters describing the dose regimen, i.e., mass of drug, frequency of administration, and route of administration. One can determine 100 possible dose regimens, for example, as defined by these three parameters: drug mass, administration frequency, administration route. One can then simulate, using the model, the drug concentration in the brain and CSF for each dose regimen. The dose regimen(s) that results in the predicted drug concentration in the brain or CSF above the desired target can then be selected for further investigation.

Figure 8:
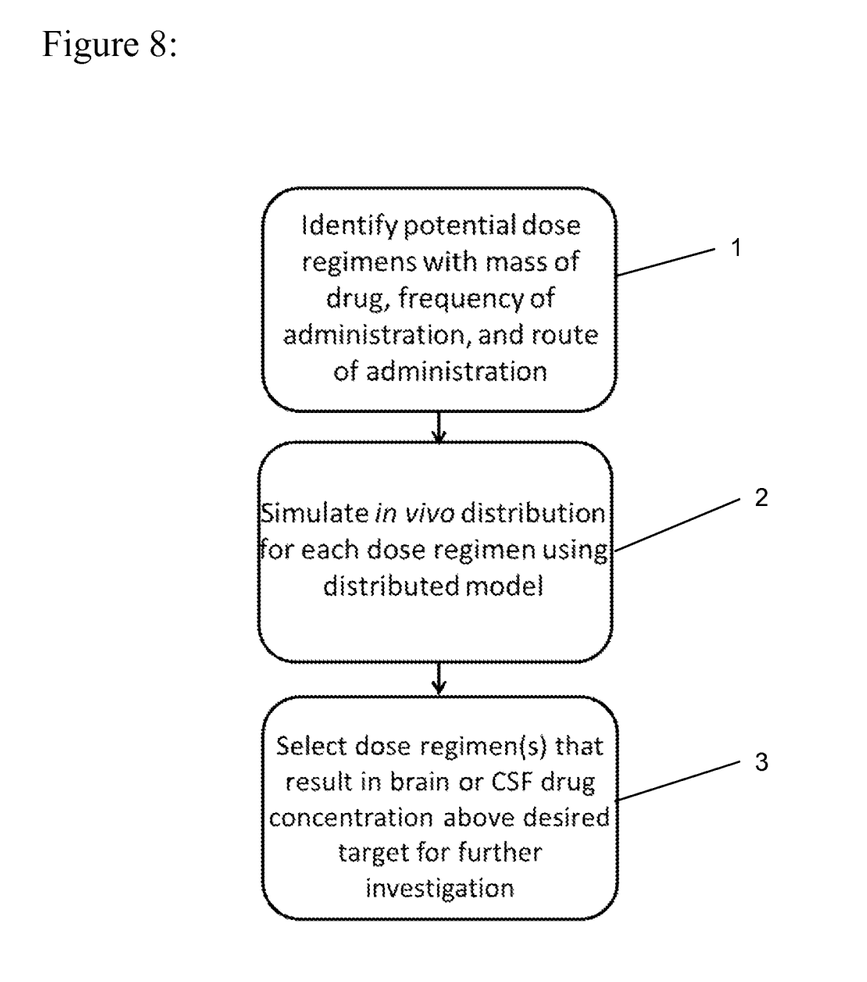
FIG. 8 is a flowchart summarizing the method to guide dose selection for human studies.

FIG. 8 is a flowchart summarizing the method to guide dose selection for human studies.

At step 1, potential dose regimens are identified with the drug mass, frequency of administration, and route of administration.

At step 2, simulations of the in vivo distribution for each dose regimen are generated using the distribution model.

At step 3, the dose regimen(s) that result in brain of CSF drug concentration above the desired target are selected for further investigation.

Figure 9:
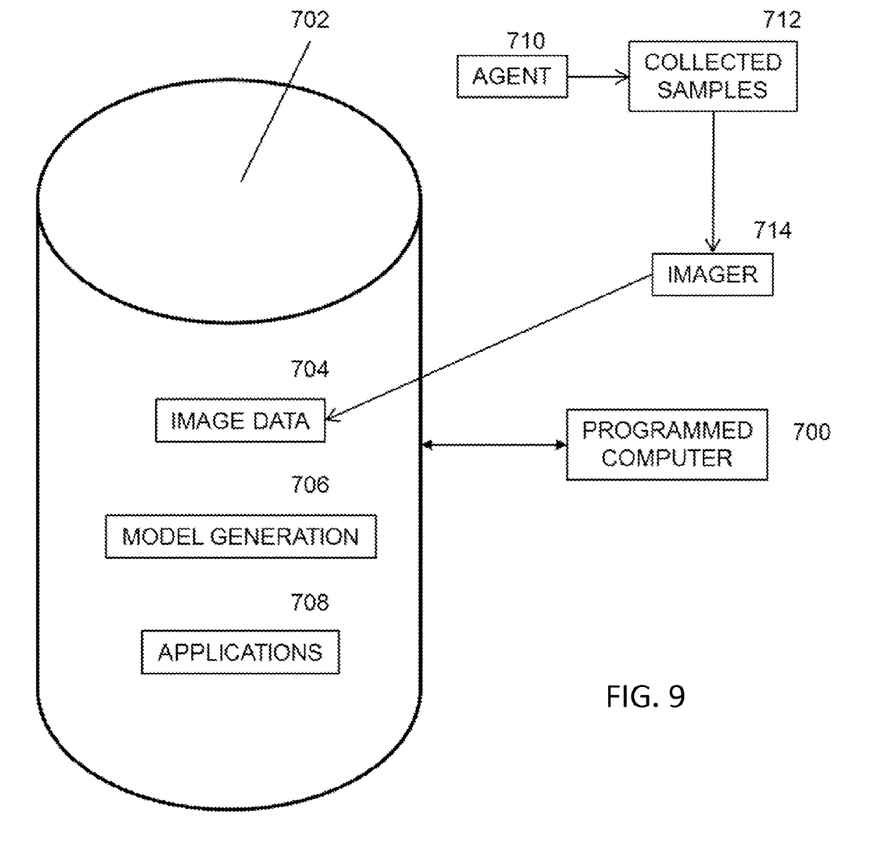
FIG. 9 is a block diagram of a computer implemented system for performing the method.

FIG. 9 is a block diagram of an apparatus for performing the method. A computer processor 700 is provided which may be a mainframe, microcomputer, embedded processor, or other processor system configured by programming to perform the computations and appropriate logical decisions described above. The processor 700 is capable of accessing one or more tangible, persistent computer readable storage medium(s) 702, which store image data 704, instructions and parameters 706 for generating the mathematical simulations described above and fitting the model to the image data to solve for one or more parameters of physiological significance, and optionally additional applications 708 for further applying the parameters of physiological significance to one or more particular problems, such as 1) use of the output data to select or reject a patient from a clinical trial (for example, using the method to determine amyloid beta density in the brain and if the density is larger than a predetermined cut off, selecting that patient for a clinical trial of a new therapeutic drug that targets amyloid beta for treating Alzheimer's disease), 2) use of the output data to diagnose a certain disease (for example, using the method to determine amyloid beta density in the brain and using the density number in the diagnosis of Alzheimer's disease), 3) use of the output data to decide on a therapeutic regimen, 4) use of the output data to track treatment of a patient and decide on additional courses of action (for example, using the method to determine amyloid beta density in the brain before and after starting a particular Alzheimer's therapy and using the two numbers to determine if the treatment should be continued or an alternative therapy should be started), or the like. These are only a few examples, which serve to illustrate without limiting the applications of the methods described herein. The image data 704 are collected by an electronic imager apparatus, such as any of the types mentioned above. The imager 714 collects the data from the samples 712 to which the CA 710 has been applied.

In some embodiments, a method of estimating a parameter of physiological significance in the central nervous system (CNS) comprises: (a) providing one or more images of the brain or cerebral spinal fluid (CSF) in a subject to whom a dose of a contrast agent (CA) has been administered; (b) determining, using a computer equipped with image processing software, the concentration or relative concentration of the agent in a region or regions of interest in the brain or CSF, thereby generating concentration data; (c) describing the time-based behavior of concentrations of CA within the brain or CSF using a pharmacokinetic model that is based on a set of pharmacokinetic model parameters; and (d) fitting, using computer code, the pharmacokinetic model to the concentration data, varying one or more parameters, wherein the best fit estimates a parameter of physiological significance in the CNS.

In some embodiments, the contrast agent includes a positron- or gamma-emitting isotope.

In some embodiments, the positron- or gamma-emitting isotope is 68Ga, 18F, 89Zr, 64Cu, 86Y, 124I, 123I, 99mTc, 125I, 111In, 67Cu, or 177Lu.

In some embodiments, the contrast agent comprises paramagnetic or superparamagnetic material.

In some embodiments, the paramagnetic or superparamagnetic material is gadolinium, iron oxide, iron platinum, or manganese.

In some embodiments, the contrast agent comprises a fluorescent probe.

In some embodiments, the one or more images are generated by single photon emission computed tomography (SPECT), positron emission tomography (PET), magnetic resonance imaging (MRI), computed tomography (CT), detecting fluorescence, or a combination thereof.

In some embodiments, the pharmacokinetic model for performing the analysis is a distributed model.

In some embodiments, the distributed model is given by the following equations:

$$\frac{\partial C(x,t)}{\partial t} = D\frac{\partial^2 C(x,t)}{\partial x^2} + \frac{PS}{V}\left(C_p(t) - \frac{C(x,t)}{\varepsilon}\right) - k_{on}\frac{C(x,t)}{\varepsilon}T(x,t) + k_{off}B(x,t)$$

$$\frac{\partial B(x,t)}{\partial t} = k_{on}\frac{C(x,t)}{\varepsilon}T(x,t) - k_{off}B(x,t) - k_{int}B(x,t)$$

$$\frac{\partial T(x,t)}{\partial t} = R_s - k_{on}\frac{C(x,t)}{\varepsilon}T(x,t) + k_{off}B(x,t) - k_{int,T}B(x,t)$$

$$\frac{\partial I(x,t)}{\partial t} = k_{int}B(x,t) - k_{resid}I(x,t)$$

$$\frac{\partial C_{CSF}(t)}{\partial t} = -\frac{Q_{CSF}}{V_{CSF}}C_{CSF}(t) + \frac{D_E A}{V_{CSF}}\frac{\partial C(0,t)}{\partial x} + \frac{P_{BCSFB}S_{BCSFB}}{V_{CSF}}(C_p(t) - C_{CSF}(t))$$

$$\frac{\partial C(L,t)}{\partial x} = 0$$

$$C_{CSF}(t) = C(0,t)$$

wherein C denotes the free CA concentration in the brain parenchyma, B denotes the bound CA/antigen concentration in the brain parenchyma, T denotes the unbound antigen concentration in the brain parenchyma, I denotes the concentration of intracellular CA, $C_{CSF}$ denotes the concentration of CA in the CSF, D denotes the CA diffusion coefficient in brain parenchyma, $k_{on}$ denotes the CA/antigen association rate constant, $k_{off}$ denotes the CA/antigen dissociation rate constant, $\varepsilon$ denotes the CA void fraction in the parenchyma, $k_{int}$ denotes the internalization rate constant of the CA/antigen bound complex, $k_{int,T}$ denotes the internalization rate constant of the antigen, $k_{resid}$ denotes the rate of release of CA or CA signal from the intracellular compartment, $R_S$ denotes the antigen synthesis rate, L denotes the half-distance of the parenchymal thickness, A denotes the ependymal surface area, P denotes the capillary to brain permeability, S denotes the capillary surface area in the brain, V denotes the brain volume, $P_{BCSFB}$ denotes the blood/CSF barrier permeability, $S_{BCSFB}$ denotes the blood/CSF surface area, $V_{CSF}$ denotes the CSF volume, $D_E$ denotes the diffusion rate across the ependymal surface, and $C_p$ denotes the plasma concentration of the contrast agent as a function of time, also sometimes called an arterial input function.

In some embodiments, the one or more parameters of physiological significance are the contrast agent affinity $K_D$, the brain permeability surface area over volume PS/V, the CSF to brain transport rate $D_E A/V_{CSF}$, the CA/antigen bound complex internalization rate $k_{int}$, and/or the antigen concentration $T_0$.

In some embodiments, a method detecting a disease lesion in a subject, the method comprises: (a) providing one or more images of a subject to whom a dose of contrast agent (CA) has been administered; (b) identifying a lesion candidate or brain region of interest based on the acquired image or images; (c) determining, using a computer equipped with image processing software, the concentration or relative concentration of the CA in a region of interest in the tissue, thereby generating concentration data; (d) describing the time-based behavior of concentrations of the CA within the subject using a pharmacokinetic model that is based on a set of pharmacokinetic model parameters; (e) fitting, using computer code, the pharmacokinetic model to the concentration data, varying one or more parameters wherein the best fit estimates a parameter or parameters of physiological significance; and (f) determining whether the lesion candidate is a disease lesion based on the concentration data and the estimated parameter or parameters of physiological significance.

In some embodiments, the pharmacokinetic model for performing the analysis is a distributed model.

In some embodiments, the one or more parameters of physiological significance are the contrast agent affinity $K_D$, the brain permeability surface area over volume PS/V, the CSF to brain transport rate $D_E A/V_{CSF}$, the CA/antigen bound complex internalization rate $k_{int}$, and/or the antigen concentration $T_0$.

In some embodiments, a computer system comprises: a processor; and a program storage device readable by the computer system, embodying a program instructions executable by the processor to perform method steps for performing pharmacokinetic analysis in image(s), the method comprising: (a) providing one or more images of a subject to whom a contrast agent (CA) has been administered; (b) identifying a lesion candidate or brain region of interest based on the one or more images; (c) determining, using a computer equipped with image processing software, the concentration or relative concentration of the CA in a region of interest in the tissue, thereby generating concentration data; (d) describing the time-based behavior of concentrations of CA within the subject using a pharmacokinetic model that is based on a set of pharmacokinetic model parameters; and (e) fitting, using computer code, the pharmacokinetic model to the concentration data, varying one or more parameters, wherein the best fit estimates a parameter or parameters of physiological significance.

In some embodiments, the pharmacokinetic model for performing pharmacokinetic analysis is a distributed model.

In some embodiments, the one or more parameters of physiological significance are is the contrast agent affinity $K_D$, the brain permeability surface area over volume PS/V, the CSF to brain transport rate $D_E A/V_{CSF}$, the CA/antigen bound complex internalization rate $k_{int}$, and/or the antigen concentration $T_0$.

The methods and system described herein may be at least partially embodied in the form of computer-implemented processes and apparatus for practicing those processes. The disclosed methods may also be at least partially embodied in the form of tangible, non-transient machine readable storage media encoded with computer program code. The media may include, for example, RAMs, ROMs, CD-ROMs, DVD-ROMs, BD-ROMs, hard disk drives, flash memories, or any other non-transient machine-readable storage medium, wherein, when the computer program code is loaded into and executed by a computer, the computer becomes an apparatus for practicing the method. The media may include one or more local and/or remotely located media devices. The methods may also be at least partially embodied in the form of a computer into which computer program code is loaded and/or executed, such that the computer becomes a special purpose apparatus for practicing the methods. When implemented on a general-purpose processor, the computer program code segments configure the processor to create specific logic circuits. The methods may alternatively be at least partially embodied in a digital signal processor formed of application specific integrated circuits for performing the methods.

Although the subject matter has been described in terms of exemplary embodiments, it is not limited thereto. Rather, the appended claims should be construed broadly, to include other variants and embodiments, which may be made by those skilled in the art.

What is claimed is:

1. A method of estimating a parameter of physiological significance in the central nervous system (CNS), the method comprising:
    (a) providing one or more images of the brain or cerebral spinal fluid (CSF) in a subject to whom a dose of a contrast agent (CA) has been administered;
    (b) determining, using a computer equipped with image processing software, the concentration or relative concentration of the CA in a region or regions of interest in the brain or CSF, thereby generating concentration data;
    (c) describing the time-based behavior of concentrations of CA within the brain or CSF using a pharmacokinetic model that is based on a set of pharmacokinetic model parameters; and
    (d) fitting, using computer code, the pharmacokinetic model to the concentration data, varying one or more parameters, wherein the best fit estimates a parameter of physiological significance in the CNS.

2. The method of claim 1, wherein the contrast agent includes a positron- or gamma-emitting isotope.

3. The method of claim 2, wherein the positron- or gamma-emitting isotope is 68Ga, 18F, 89Zr, 64Cu, 86Y, 124I, 123I, 99mTc, 125I, 111In, 67Cu, or 177Lu.

4. The method of claim 1, wherein the contrast agent comprises paramagnetic or superparamagnetic material.

5. The method of claim 4, wherein the paramagnetic or superparamagnetic material is gadolinium, iron oxide, iron platinum, or manganese.

6. The method of claim 1, wherein the contrast agent comprises a fluorescent probe.

7. The method of claim 1, wherein the one or more images are generated by single photon emission computed tomography (SPECT), positron emission tomography (PET), magnetic resonance imaging (MRI), computed tomography (CT), detecting fluorescence, or a combination thereof.

8. The method of claim 1, wherein the pharmacokinetic model for performing the analysis is a distributed model.

9. The method of claim 8, wherein the distributed model is given by the following equations:

$$\frac{\partial C(x,t)}{\partial t} = D\frac{\partial^2 C(x,t)}{\partial x^2} + \frac{PS}{V}\left(C_p(t) - \frac{C(x,t)}{\varepsilon}\right) - k_{on}\frac{C(x,t)}{\varepsilon}T(x,t) + k_{off}B(x,t)$$

$$\frac{\partial B(x,t)}{\partial t} = k_{on}\frac{C(x,t)}{\varepsilon}T(x,t) - k_{off}B(x,t) - k_{int}B(x,t)$$

-continued $$\frac{\partial T(x, t)}{\partial t} = R_s - k_{on}\frac{C(x, t)}{\varepsilon}T(x, t) + k_{off}B(x, t) - k_{int,T}B(x, t)$$

$$\frac{\partial I(x, t)}{\partial t} = k_{int}B(x, t) - k_{resid}I(x, t)$$

$$\frac{\partial C_{CSF}(t)}{\partial t} =$$

$$-\frac{Q_{CSF}}{V_{CSF}}C_{CSF}(t) + \frac{D_E A}{V_{CSF}}\frac{\partial C(0, t)}{\partial x} + \frac{P_{BCSFB}S_{BCSFB}}{V_{CSF}}(C_p(t) - C_{CSF}(t))$$

$$\frac{\partial C(L, t)}{\partial x} = 0$$

$$C_{CSF}(t) = C(0, t)$$

wherein C denotes the free CA concentration in the brain parenchyma, B denotes the bound CA/antigen concentration in the brain parenchyma, T denotes the unbound antigen concentration in the brain parenchyma, I denotes the concentration of intracellular CA, $C_{CSF}$ denotes the concentration of CA in the CSF, D denotes the CA diffusion coefficient in brain parenchyma, $k_{on}$ denotes the CA/antigen association rate constant, $k_{off}$ denotes the CA/antigen dissociation rate constant, $\varepsilon$ denotes the CA void fraction in the parenchyma, $k_{int}$ denotes the internalization rate constant of the CA/antigen bound complex, $k_{int,T}$ denotes the internalization rate constant of the antigen, $k_{resid}$ denotes the rate of release of CA or CA signal from the intracellular compartment, $R_S$ denotes the antigen synthesis rate, L denotes the half-distance of the parenchymal thickness, A denotes the ependymal surface area, P denotes the capillary to brain permeability, S denotes the capillary surface area in the brain, V denotes the brain volume, $P_{BCSFB}$ denotes the blood/CSF barrier permeability, $S_{BCSFB}$ denotes the blood/CSF surface area, $V_{CSF}$ denotes the CSF volume, $D_E$ denotes the diffusion rate across the ependymal surface, and $C_p$ denotes the plasma concentration of the contrast agent as a function of time, also sometimes called an arterial input function.

10. The method of claim 1, wherein the one or more parameters of physiological significance are the contrast agent affinity $K_D$, the brain permeability surface area over volume PS/V, the CSF to brain transport rate $D_E A/V_{CSF}$, the CA/antigen bound complex internalization rate $k_{int}$, and/or the antigen concentration $T_0$.

11. A method detecting a disease lesion in a subject, the method comprising:
(a) providing one or more images of a subject to whom a dose of contrast agent (CA) has been administered;
(b) identifying a lesion candidate or brain region of interest based on the one or more images;
(c) determining, using a computer equipped with image processing software, the concentration or relative concentration of the CA in a region of interest in the tissue, thereby generating concentration data;
(d) describing the time-based behavior of concentrations of the CA within the subject using a pharmacokinetic model that is based on a set of pharmacokinetic model parameters;
(e) fitting, using computer code, the pharmacokinetic model to the concentration data, varying one or more parameters wherein the best fit estimates a parameter or parameters of physiological significance; and
(f) determining whether the lesion candidate is a disease lesion based on the concentration data and the estimated parameter or parameters of physiological significance.

12. The method of claim 11, wherein the pharmacokinetic model for performing the analysis is a distributed model.

13. The method of claim 12, wherein the distributed model is given by the following equations:

$$\frac{\partial C(x, t)}{\partial t} =$$

$$D\frac{\partial^2 C(x, t)}{\partial x^2} + \frac{PS}{V}\left(C_p(t) - \frac{C(x, t)}{\varepsilon}\right) - k_{on}\frac{C(x, t)}{\varepsilon}T(x, t) + k_{off}B(x, t)$$

$$\frac{\partial B(x, t)}{\partial t} = k_{on}\frac{C(x, t)}{\varepsilon}T(x, t) - k_{off}B(x, t) - k_{int}B(x, t)$$

$$\frac{\partial T(x, t)}{\partial t} = R_s - k_{on}\frac{C(x, t)}{\varepsilon}T(x, t) + k_{off}B(x, t) - k_{int,T}B(x, t)$$

$$\frac{\partial I(x, t)}{\partial t} = k_{int}B(x, t) - k_{resid}I(x, t)$$

$$\frac{\partial C_{CSF}(t)}{\partial t} =$$

$$-\frac{Q_{CSF}}{V_{CSF}}C_{CSF}(t) + \frac{D_E A}{V_{CSF}}\frac{\partial C(0, t)}{\partial x} + \frac{P_{BCSFB}S_{BCSFB}}{V_{CSF}}(C_p(t) - C_{CSF}(t))$$

$$\frac{\partial C(L, t)}{\partial x} = 0$$

$$C_{CSF}(t) = C(0, t)$$

wherein C denotes the free CA concentration in the brain parenchyma, B denotes the bound CA/antigen concentration in the brain parenchyma, T denotes the unbound antigen concentration in the brain parenchyma, I denotes the concentration of intracellular CA, $C_{CSF}$ denotes the concentration of CA in the CSF, D denotes the CA diffusion coefficient in brain parenchyma, $k_{on}$ denotes the CA/antigen association rate constant, $k_{off}$ denotes the CA/antigen dissociation rate constant, $\varepsilon$ denotes the CA void fraction in the parenchyma, $k_{int}$ denotes the internalization rate constant of the CA/antigen bound complex, $k_{int,T}$ denotes the internalization rate constant of the antigen, $k_{resid}$ denotes the rate of release of CA or CA signal from the intracellular compartment, $R_S$ denotes the antigen synthesis rate, L denotes the half-distance of the parenchymal thickness, A denotes the ependymal surface area, P denotes the capillary to brain permeability, S denotes the capillary surface area in the brain, V denotes the brain volume, $P_{BCSFB}$ denotes the blood/CSF barrier permeability, $S_{BCSFB}$ denotes the blood/CSF surface area, $V_{CSF}$ denotes the CSF volume, $D_E$ denotes the diffusion rate across the ependymal surface, and $C_p$ denotes the plasma concentration of the contrast agent as a function of time, also sometimes called an arterial input function.

14. The method of claim 11, where the one or more parameters of physiological significance are the contrast agent affinity $K_D$, the brain permeability surface area over volume PS/V, the CSF to brain transport rate $D_E A/V_{CSF}$, the CA/antigen bound complex internalization rate $k_{int}$, and/or the antigen concentration $T_0$.

15. A computer system comprising: a processor; and a program storage device readable by the computer system, embodying a program instructions executable by the processor to perform method steps for performing pharmacokinetic analysis in image(s), the method comprising:

(a) providing one or more images of a subject to whom a contrast agent (CA) has been administered;
(b) identifying a lesion candidate or brain region of interest based on the one or more images;
(c) determining, using a computer equipped with image processing software, the concentration or relative concentration of the CA in a region of interest in the tissue, thereby generating concentration data;
(d) describing the time-based behavior of concentrations of CA within the subject using a pharmacokinetic model that is based on a set of pharmacokinetic model parameters; and
(e) fitting, using computer code, the pharmacokinetic model to the concentration data, varying one or more parameters, wherein the best fit estimates a parameter or parameters of physiological significance.

16. The computer system of claim 15, wherein the pharmacokinetic model for performing pharmacokinetic analysis is a distributed model.

17. The method of claim 16, wherein the distributed model is given by the following equations:

$$\frac{\partial C(x,t)}{\partial t} = D\frac{\partial^2 C(x,t)}{\partial x^2} + \frac{PS}{V}\left(C_p(t) - \frac{C(x,t)}{\varepsilon}\right) - k_{on}\frac{C(x,t)}{\varepsilon}T(x,t) + k_{off}B(x,t)$$

$$\frac{\partial B(x,t)}{\partial t} = k_{on}\frac{C(x,t)}{\varepsilon}T(x,t) - k_{off}B(x,t) - k_{int}B(x,t)$$

$$\frac{\partial T(x,t)}{\partial t} = R_s - k_{on}\frac{C(x,t)}{\varepsilon}T(x,t) + k_{off}B(x,t) - k_{int,T}B(x,t)$$

$$\frac{\partial I(x,t)}{\partial t} = k_{int}B(x,t) - k_{resid}I(x,t)$$

$$\frac{\partial C_{CSF}(t)}{\partial t} = -\frac{Q_{CSF}}{V_{CSF}}C_{CSF}(t) + \frac{D_E A}{V_{CSF}}\frac{\partial C(0,t)}{\partial x} + \frac{P_{BCSFB}S_{BCSFB}}{V_{CSF}}(C_p(t) - C_{CSF}(t))$$

$$\frac{\partial C(L,t)}{\partial x} = 0$$

$$C_{CSF}(t) = C(0,t)$$

wherein C denotes the free CA concentration in the brain parenchyma, B denotes the bound CA/antigen concentration in the brain parenchyma, T denotes the unbound antigen concentration in the brain parenchyma, I denotes the concentration of intracellular CA, $C_{CSF}$ denotes the concentration of CA in the CSF, D denotes the CA diffusion coefficient in brain parenchyma, $k_{on}$ denotes the CA/antigen association rate constant, $k_{off}$ denotes the CA/antigen dissociation rate constant, $\varepsilon$ denotes the CA void fraction in the parenchyma, $k_{int}$ denotes the internalization rate constant of the CA/antigen bound complex, $k_{int,T}$ denotes the internalization rate constant of the antigen, $k_{resid}$ denotes the rate of release of CA or CA signal from the intracellular compartment, $R_S$ denotes the antigen synthesis rate, L denotes the half-distance of the parenchymal thickness, A denotes the ependymal surface area, P denotes the capillary to brain permeability, S denotes the capillary surface area in the brain, V denotes the brain volume, $P_{BCSFB}$ denotes the blood/CSF barrier permeability, $S_{BCSFB}$ denotes the blood/CSF surface area, $V_{CSF}$ denotes the CSF volume, $D_E$ denotes the diffusion rate across the ependymal surface, and $C_p$ denotes the plasma concentration of the contrast agent as a function of time, also sometimes called an arterial input function.

18. The computer system of claim 17, wherein the one or more parameters of physiological significance are is the contrast agent affinity $K_D$, the brain permeability surface area over volume PS/V, the CSF to brain transport rate $D_E A/V_{CSF}$, the CA/antigen bound complex internalization rate $k_{int}$, and/or the antigen concentration $T_0$.

* * * * *